(12) United States Patent
Schneider

(10) Patent No.: US 6,648,741 B2
(45) Date of Patent: Nov. 18, 2003

(54) APPARATUS FOR PROTECTING THE EDGE GEOMETRY OF AN INTRAOCULAR LENS DURING GLASS BEAD POLISHING PROCESS

(75) Inventor: Ned E. Schneider, Aliso Viejo, CA (US)

(73) Assignee: Advanced Medical Optics, Inc., Sana Ana, CA (US)

(*) Notice: Subject to any disclaimer, the term of this patent is extended or adjusted under 35 U.S.C. 154(b) by 0 days.

(21) Appl. No.: 10/099,067

(22) Filed: Mar. 14, 2002

(65) Prior Publication Data
US 2003/0176918 A1 Sep. 18, 2003

(51) Int. Cl.$^7$ .............................. B24B 13/00; A61F 2/16
(52) U.S. Cl. .................. 451/390; 264/2.7; 623/6.16; 623/6.17
(58) Field of Search ..................... 451/42, 390, 35, 451/384; 264/2.7, 1.1; 623/6.16, 6.17

(56) References Cited

U.S. PATENT DOCUMENTS

| | | |
|---|---|---|
| 2,043,840 A | 6/1936 | Singer |
| 3,034,403 A | 5/1962 | Neefe |
| 3,454,332 A | 7/1969 | Siegel |
| 4,435,856 A | 3/1984 | L'Esperance |
| 4,449,257 A | 5/1984 | Koeniger |
| 4,451,938 A | 6/1984 | Kelman |
| 4,580,371 A * | 4/1986 | Akhavi .................. 451/32 |
| 4,601,722 A | 7/1986 | Kelman |
| 4,605,409 A | 8/1986 | Kelman |
| 4,676,791 A | 6/1987 | LeMaster et al. |
| 4,702,244 A | 10/1987 | Mazzocco |
| 4,738,680 A | 4/1988 | Herman |
| 4,743,254 A | 5/1988 | Davenport |
| 4,781,717 A | 11/1988 | Grendahl |
| 4,808,181 A | 2/1989 | Kelman |

(List continued on next page.)

FOREIGN PATENT DOCUMENTS

| | | |
|---|---|---|
| EP | 0246754 | 11/1987 |
| EP | 0419740 | 4/1991 |
| EP | 0457553 | 11/1991 |
| EP | 0458508 | 11/1991 |
| EP | 0507292 | 10/1992 |
| EP | 0599457 | 6/1994 |
| EP | 0668061 | 8/1995 |
| EP | 0916320 | 5/1999 |
| FR | 2661816 | 11/1991 |
| FR | 2668922 | 5/1992 |
| GB | 2181355 | 4/1987 |
| WO | 83/01566 | 5/1983 |
| WO | 89/09576 | 10/1989 |
| WO | 92/08422 | 5/1992 |
| WO | 93/00204 | 1/1993 |
| WO | 97/33536 | 9/1997 |

OTHER PUBLICATIONS

Guttman, Opthalmology Time, Jun. 15, 1999.
Charters, Ophthalmology Times, Jun. 15, 1999.
Beiting, Eye World, Jun. 1999.
Nishi, Ocul Surg News, Jul. 1, 1999, p. 45.

(List continued on next page.)

Primary Examiner—David H. Willse
Assistant Examiner—Suzette J. Jackson
(74) Attorney, Agent, or Firm—Stout, Uxa, Buyan & Mullins, LLP; Frank Uxa; Peter John Gluck

(57) ABSTRACT

Apparatus and methods for protecting the edge geometry of an intraocular lens during polishing are disclosed. The apparatus comprises a protective device having a cavity configured to receive the lens and an annular peripheral portion for surrounding and protecting at least one edge corner of the lens. In one embodiment, the peripheral portion has a constant inner diameter and receives the lens in an interference fit. In another embodiment, the lens is trapped between flanges which extend radially inwardly from the peripheral portion. A lens that is encased in the protective device will have a polished central portion and an unpolished peripheral portion after the polishing process has been completed and the protective device has been removed.

8 Claims, 1 Drawing Sheet

U.S. PATENT DOCUMENTS

| | | | |
|---|---|---|---|
| 4,856,234 A | * | 8/1989 | Goins ........................ 451/42 |
| 5,002,571 A | | 3/1991 | O'Donnell, Jr. et al. |
| 5,011,494 A | | 4/1991 | von Recum et al. |
| 5,074,875 A | | 12/1991 | Donn et al. |
| 5,076,684 A | | 12/1991 | Simpson et al. |
| 5,089,023 A | | 2/1992 | Swanson |
| 5,171,320 A | | 12/1992 | Nishi |
| 5,366,501 A | | 11/1994 | Langerman |
| 5,370,687 A | | 12/1994 | Poler |
| 5,405,385 A | | 4/1995 | Heimke et al. |
| 5,429,838 A | * | 7/1995 | Mansson et al. ........... 427/2.24 |
| 5,549,670 A | | 8/1996 | Young et al. |
| 5,674,283 A | | 10/1997 | Stoy |
| 5,693,093 A | | 12/1997 | Woffinden et al. |
| 5,693,094 A | | 12/1997 | Young et al. |
| 5,725,811 A | * | 3/1998 | Nguyen et al. .............. 264/2.7 |
| 5,755,786 A | | 5/1998 | Woffinden et al. |
| 5,961,370 A | * | 10/1999 | Valle et al. .................... 451/35 |
| 6,010,391 A | * | 1/2000 | Lewellen et al. ............. 451/35 |
| 6,162,249 A | * | 12/2000 | Deacon et al. ............. 623/6.16 |
| 6,258,123 B1 | * | 7/2001 | Young et al. .............. 623/6.16 |
| 6,432,246 B1 | * | 8/2002 | Blake ........................ 156/245 |
| 6,468,306 B1 | * | 10/2002 | Paul et al. ................. 623/6.16 |

OTHER PUBLICATIONS

Holladay et al, J Cataract Refract Surg. Jun. 1999, pp. 748–752.
Apple, Ocular Surgery News, 1999.
Cataract Refractive Surg., Vol 18, pp. 333–341, Jul. 1992.
Coombes & Seward, Br J Ophthalmol, 1999.
Experimental Cell Research 167 (1986) pp. 203–217.
Masket et al, J Cataract Refract Surg, Nov. 1993, pp. 690–694.
Choyce, Rayner & Keeler Limited, Catalogue No. 469, 7/78.
Waller & Steinert, Am. Journal of Ophthalmology, Sep. 1993, pp. 374–375.
Nishi et al, Ophthalmic Surgery and Lasers, Jul. 1998, pp. 587–593.
Nagata & Watanabe, Jpn J Ophthalmol, 1996, pp. 397–403.
Peng et al, Chicago Ophthalmology Society Meeting, Oct. 20–21, 1997.
Nishi & Nishi, J Cataract Refract Surg, Apr. 1999, pp. 521–526.
2110724, Jan. 1990, Database WPI.

* cited by examiner

APPARATUS FOR PROTECTING THE EDGE GEOMETRY OF AN INTRAOCULAR LENS DURING GLASS BEAD POLISHING PROCESS

BACKGROUND OF THE INVENTION

This invention relates to apparatus and methods for manufacturing intraocular lenses (IOLs). More particularly, the application relates to an apparatus for protecting the edge geometry of an IOL during the polishing process.

An intraocular lens is commonly used to replace the natural lens of a human eye when warranted by medical conditions. Often, an IOL is implanted in a region of the eye known as the capsular bag or posterior capsule.

One problem frequently associated with IOLs is the phenomenon of posterior capsule opacification (PCO), in which epithelial cells from the posterior capsule tend to grow in front of and/or behind the optic of the IOL. This tends to block the optic and to impair vision.

Another concern with IOLs is glare. Light tends to reflect off the edges of the IOL, which can annoy the patient. In some cases, edge glare can be so irritating that the IOL must be removed and replaced.

A new generation of IOLs has been developed to obviate the problems of PCO and edge glare. Specifically, the new IOLs have been provided with special edge configurations which inhibit the growth of epithelial cells around the lens and reduce the amount of light reflected toward the optical axis. Examples of such edge configurations are shown in U.S. Pat. No. 6,162,249 to Deacon et al, the disclosure of which in its entirety is hereby incorporated by reference.

The new-generation IOLs may be manufactured using any convenient technique. Typically, they are lathed from blanks of polymerized lens material, and then polished to a desired optical finish. A preferred polishing method involves tumbling a lens cryogenically in a vessel filled with glass beads and polishing fluid. During this process, the sharp posterior edge of the lens tends to become rounded and indistinct. One solution to this problem is to mask the edge during polishing, but no apparatus for efficiently and uniformly masking an IOL edge has been discovered until now.

It would be advantageous, therefore, to provide an apparatus and method for protecting the edge geometry of an IOL during polishing.

SUMMARY OF THE INVENTION

A method and apparatus for protecting the edge geometry of an IOL during polishing have been discovered. Specifically, the method comprises encasing a peripheral portion of an IOL in a protective device before placement in a polishing apparatus such as a tumbler.

The protective device comprises a solid body having a cavity for receiving the IOL, and a peripheral portion for surrounding and protecting the edge of the IOL. Preferably, the solid body is made of a relatively durable material, such as cast acrylic, which allows it to be used more than once before disposal.

In one embodiment of the invention, the solid body comprises an annulus having a constant inner diameter slightly less than the outer diameter of the IOL. Thus, the annulus receives the IOL in an interference fit.

In another embodiment of the invention, the solid body comprises an annulus having retaining members and a receiving portion. The retaining members include a first projection extending radially inwardly along the inner circumference of the annulus proximate the top surface and a second projection extending radially inwardly along the inner circumference of the annulus proximate the bottom surface. The receiving portion extends longitudinally between the top and bottom surfaces and has an inner diameter approximately equal to the outer diameter of the IOL. The IOL is captured between the first and second projections.

Each and every feature described herein, and each and every combination of two or more of such features, is included within the scope of the present invention provided that the features included in such a combination are not mutually inconsistent.

The invention, together with additional features and advantages thereof, may best be understood by reference to the following description taken in connection with the accompanying illustrative drawings in which like parts bear like reference numerals.

DESCRIPTION OF THE PREFERRED EMBODIMENTS

Figure 2:
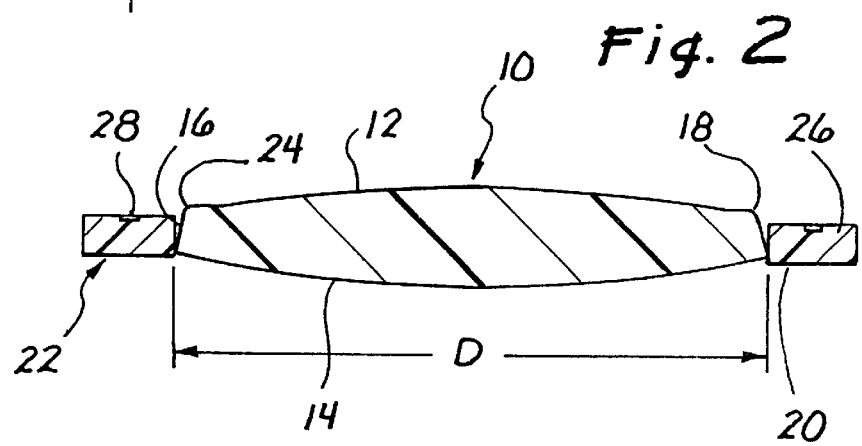
FIG. 2 is a cross-sectional view of the device shown in FIG. 1 encasing an intraocular lens.
Figure 3:
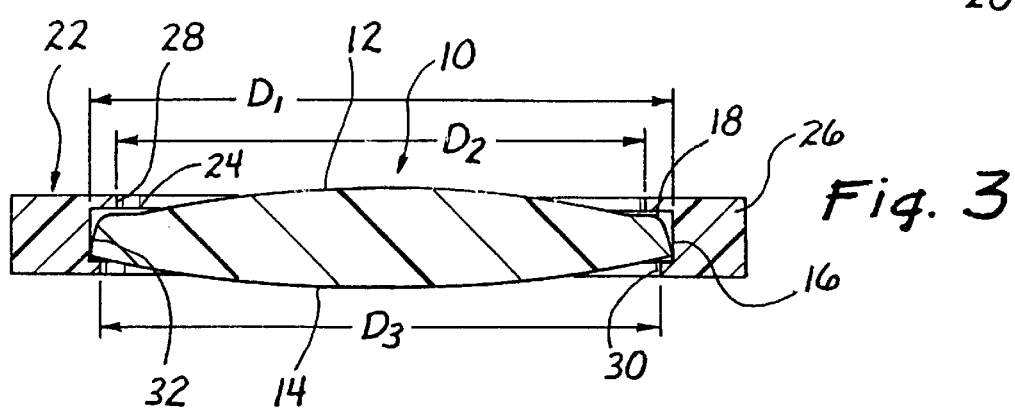
FIG. 3 is a cross-sectional view, similar to FIG. 2, showing an alternate embodiment of the protective device.

The optic 10 of an exemplary IOL having an edge geometry for inhibiting cell growth and reducing glare is shown in cross-section in FIGS. 2 and 3. The optic 10 includes a convex anterior surface 12 and a convex posterior surface 14. The surfaces 12 and 14 are connected by a circumferentially extending edge surface 16. An anterior edge corner 18 is formed at the intersection of the edge surface 16 and the anterior surface 12. A posterior edge corner 20 is formed at the intersection of the edge surface 16 and the posterior surface 14. The anterior edge corner 18 is somewhat rounded, while the posterior edge corner 20 is sharp and must remain so. The particular edge configuration shown is not meant to be limiting, however, as the principles of the instant invention can be applied to optics having any edge configuration which is susceptible to rounding or other damage.

Figure 1:
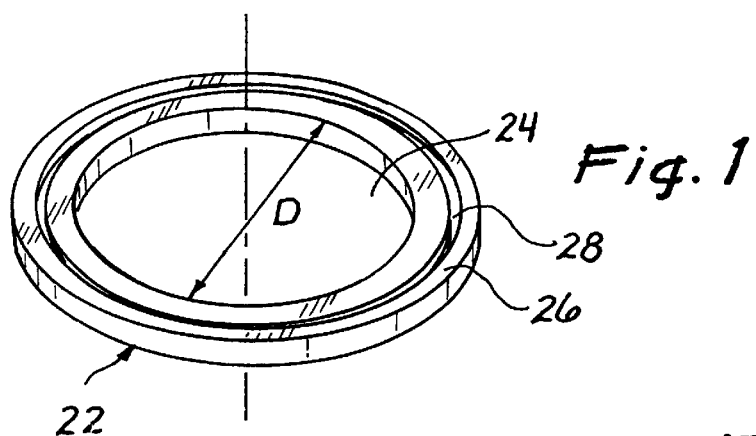
FIG. 1 is a perspective view from the top showing one embodiment of a protective device according to the present invention.

The optic 10 may be manufactured using any convenient technique, but is typically lathed from a blank of rigid polymerized lens material such as polymethyl acrylate (PMMA), or resiliently deformable polymerized lens material, such as silicone polymeric materials, acrylic polymeric materials, hydrogel-forming polymeric materials, and mixtures thereof. After lathing, the optic 10 is polished by cryogenic tumbling in a vessel containing glass beads and polishing fluid. In the method according to the present invention, the edge geometry of the optic is protected during polishing by encasing a peripheral portion of the optic in a protective device 22, one embodiment of which is shown in FIGS. 1 and 2.

The protective device 22 comprises a solid body having a cavity 24 for receiving the optic 10, and a peripheral portion 26 for surrounding and protecting at least one of the edge corners 18, 20 of the optic 10. In the illustrated embodiment, the sharp posterior edge corner 20 requires protection and is therefore completely encased in the protective device 22, while the blunt anterior edge corner 18 projects above the peripheral portion 26.

The shape and dimensions of the cavity 24 are selected to enable the cavity to receive the outermost edge of the optic 10 in an interference fit. In the case of a typical optic which is circular in plan and has a diameter of about 0.236", the cavity 24 is also circular and has a diameter D of about 0.2341" to 0.235". It is therefore necessary to compress the optic slightly when inserting it into the cavity 24. This can be done either manually or with an insertion tool, the particulars of which do not fall within the scope of the present invention but can be readily ascertained by a practitioner skilled in the mechanical arts.

The peripheral portion 26, which is shown here as an annulus or ring, is preferably formed of sufficiently durable material to withstand multiple cycles in a glass bead polishing apparatus. One material which has been found to be suitable is cast acrylic. To ensure that the apparatus 22 is not reused excessively, a wear ring or groove 28 is formed in one surface of the peripheral portion 26. The depth of the wear ring 28, which is initially about 0.0015" in a peripheral portion about 0.0131" thick, decreases as the amount of wear on the device 22 increases, thus providing a visual indication of the condition of the device 22. When the wear ring 28 is no longer visible, the device 22 should be disposed of.

Figure 4:
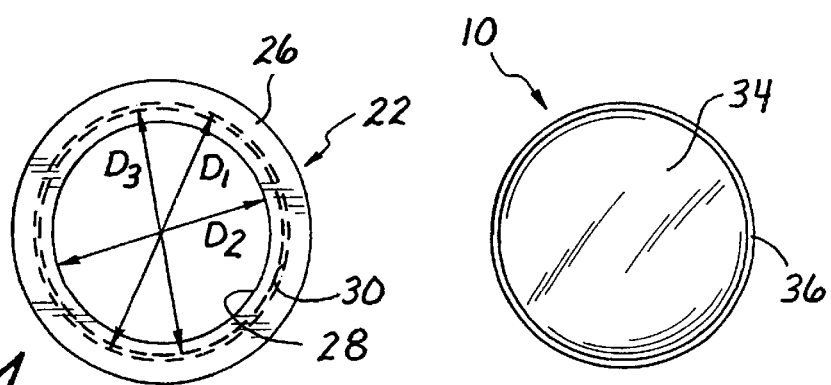
FIG. 4 is a top plan view of the protective device shown in FIG. 3.

An alternate embodiment of the device 22', shown in FIGS. 3 and 4, does not require mechanical interference between the inner diameter of the peripheral portion 26' and the outermost edge of the optic. Instead, the optic 10 is trapped between retaining members 28 and 30 that extend radially inwardly from the top and bottom surfaces, respectively, of the device 22'. While the retaining members 28 and 30 are shown here as continuous circumferentially extending flanges, any type of inwardly projecting structures, such as a plurality of circumferentially spaced apart beads, would serve the same purpose.

In the illustrated embodiment, the top retaining member 28 extends farther inward than the bottom retaining member 30, since the anterior surface 12 of the optic 10 is effectively smaller in diameter than the posterior surface 14. Thus, the inner diameter of the peripheral portion 26 varies at different axial locations along the device 22'. For example, in a device 22' designed to accommodate an optic having a diameter of 0.236", the inner diameter D, at the axial center 32 of the peripheral portion 26' is about 0.235" to 236", while the inner diameter $D_2$ at the top surface of the peripheral portion 26' is 0.2141", and the inner diameter $D_3$ at the bottom surface of the peripheral portion 26' is 0.228". In this embodiment, it is not only the sharp posterior edge corner 20 of the optic which is encased in the protective device 22, but the blunt anterior edge corner 18 as well.

Figure 5:
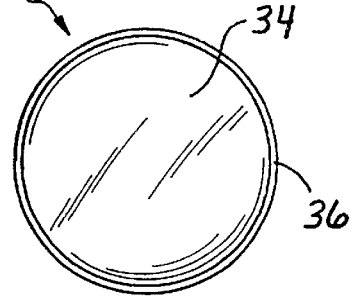
FIG. 5 is a top plan view showing an intraocular lens which has been polished using the method of the present invention after the protective device has been removed.

FIG. 5 shows an optic 10 that has been polished using a protective device 22 according to the present invention. The central portion 34 of the optic 10, which was exposed during the tumbling process, is smooth and shiny, while a small peripheral portion 36, which was protected by the device 22, is dull. In an optic 10 encased in the embodiment of the device 22 shown in FIGS. 1 and 2, the polished central portion 34 comprises substantially all of the anterior surface 12 and substantially all of the posterior surface 14 of the optic 10, plus the anterior edge corner 18 and a portion of the edge surface 16. Only a small part of the edge surface 16 adjacent the sharp posterior edge corner 20 is unpolished. If the device 22' shown in the alternate embodiment of FIGS. 3 and 4 is used, the unpolished peripheral portion 36 is somewhat larger, encompassing substantially the entire edge surface 16, the anterior and posterior edge corners 18, 20, and peripheral sections of both the anterior surface 12 and the posterior surface 14.

While this invention has been described with respect to various specific examples and embodiments, it is to be understood that the invention is not limited thereto and that it can be variously practiced within the scope of the following claims.

What is claimed is:

1. A combination comprising:

an intraocular lens having an anterior surface, a posterior surface, and a peripheral edge having at least a portion susceptible to rounding; and an apparatus positioned relative the lens for protecting at least the susceptible portion of the peripheral edge during polishing of the anterior and posterior surfaces.

2. The combination according to claim 1, wherein the apparatus comprises a solid body having a cavity for receiving the lens and a peripheral portion for surrounding and protecting at least the susceptible portion of the edge of the lens.

3. The combination of claim 2, wherein:

the intraocular lens includes an optic having a perimeter of predetermined shape; and the cavity has a shape matching the perimeter of the optic.

4. The combination of claim 3, wherein the cavity has an inner diameter dimensioned to receive the perimeter of the intraocular lens in an interference fit.

5. The combination of claim 4, further comprising retaining means positioned relative the solid body for retaining the lens within the cavity.

6. The combination of claim 5, wherein the retaining means comprises portions of the peripheral portion of the solid body configured to extend over anterior and posterior surfaces of the lens to retain the lens within the cavity.

7. The combination of claim 6, wherein the retaining means comprises at least a first projection extending into the cavity adjacent a first surface of the solid body and at least a second projection extending into the cavity adjacent a second surface of the solid body, wherein the perimeter of the lens is entrapped between the first and second projections.

8. The combination of claim 3, wherein:

wherein the peripheral edge includes at least one peripheral edge surface having a linear cross-section; and the susceptible portion of the peripheral edge comprises at least one sharp edge corner formed between the at least one peripheral edge surface and least one of the anterior and posterior surfaces.

* * * * *

UNITED STATES PATENT AND TRADEMARK OFFICE
CERTIFICATE OF CORRECTION

PATENT NO. : 6,648,741 B2
DATED : November 18, 2003
INVENTOR(S) : Ned E. Schneider It is certified that error appears in the above-identified patent and that said Letters Patent is hereby corrected as shown below:

<u>Column 3,</u>
Line 14, "0.2341" should read -- 0.234 --.
Line 28, "0.0131" should read -- 0.013 --.
Line 51, "D" should read $D_1$ --.
Line 54, "0.2141" should read -- 0.214 --.

Signed and Sealed this

Fifteenth Day of June, 2004

JON W. DUDAS
*Acting Director of the United States Patent and Trademark Office*